United States Patent
Lim et al.

(10) Patent No.: US 10,756,276 B2
(45) Date of Patent: Aug. 25, 2020

(54) ORGANIC PHOTODIODE AND ORGANIC IMAGE SENSOR INCLUDING THE SAME

(71) Applicant: LG CHEM, LTD., Seoul (KR)

(72) Inventors: Bogyu Lim, Daejeon (KR); Sang Ah Kim, Daejeon (KR); Ji Hoon Kim, Daejeon (KR); Seung Jun Yoo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 16/472,508

(22) PCT Filed: Sep. 17, 2018

(86) PCT No.: PCT/KR2018/010895
§ 371 (c)(1),
(2) Date: Jun. 21, 2019

(87) PCT Pub. No.: WO2019/078491
PCT Pub. Date: Apr. 25, 2019

(65) Prior Publication Data
US 2020/0194680 A1 Jun. 18, 2020

(30) Foreign Application Priority Data

Oct. 18, 2017 (KR) .................. 10-2017-0135199
Sep. 14, 2018 (KR) .................. 10-2018-0110129

(51) Int. Cl.
*H01L 51/00* (2006.01)
*H01L 51/42* (2006.01)

(52) U.S. Cl.
CPC ...... *H01L 51/0067* (2013.01); *H01L 51/0069* (2013.01); *H01L 51/0074* (2013.01); *H01L 51/4253* (2013.01)

(58) Field of Classification Search
CPC ............ H01L 51/0067; H01L 51/0069; H01L 51/0074; H01L 51/4253
See application file for complete search history.

(56) References Cited

U.S. PATENT DOCUMENTS 6,143,433 A * 11/2000 Murata .................. H05B 33/10
428/690
7,445,855 B2 * 11/2008 Mackenzie ........... C07F 15/006
428/690

(Continued)

FOREIGN PATENT DOCUMENTS

JP 2016065218 4/2016
KR 20130047367 5/2013

(Continued)

OTHER PUBLICATIONS

International Search Report of the International Searching Authority corresponding to International Patent Application No. PCT/KR2018/010895, dated Jan. 2, 2019. (5 pages with English translation).

*Primary Examiner* — Ida M Soward
(74) *Attorney, Agent, or Firm* — Myers Bigel, P.A.

(57) ABSTRACT

The present specification relates to an organic photodiode including: a first electrode; a second electrode provided to face the first electrode; and an organic material layer having one or more layers provided between the first electrode and the second electrode, in which one or more layers of the organic material layer include the compound of Formula 1, and an organic image sensor including the same.

13 Claims, 4 Drawing Sheets

(56) References Cited

U.S. PATENT DOCUMENTS

| | | | |
|---|---|---|---|
| 8,007,926 B2* | 8/2011 | Thompson | C07F 15/0086 |
| | | | 428/690 |
| 9,190,626 B2* | 11/2015 | Joo | H01L 51/5068 |
| 9,391,281 B2* | 7/2016 | Lee | C07D 403/10 |
| 9,540,374 B2* | 1/2017 | Park | C09K 11/06 |
| 9,748,489 B2* | 8/2017 | Kim | C08G 61/126 |
| 9,954,181 B2* | 4/2018 | Heo | H01L 51/0067 |
| 10,326,083 B2* | 6/2019 | Yagi | C07D 421/04 |
| 10,381,569 B2* | 8/2019 | Xia | H01L 51/0071 |
| 10,662,313 B2* | 5/2020 | Choi | H01L 51/4246 |
| 2011/0049367 A1* | 3/2011 | Forrest | H01L 51/0035 |
| | | | 250/338.4 |
| 2013/0042918 A1* | 2/2013 | Evans | C07D 495/04 |
| | | | 136/263 |
| 2013/0105768 A1 | 5/2013 | Leem et al. | |
| 2014/0131627 A1 | 5/2014 | Wang et al. | |
| 2016/0372680 A1 | 12/2016 | Lim et al. | |
| 2017/0210752 A1 | 7/2017 | Mitchell et al. | |

FOREIGN PATENT DOCUMENTS

| | | |
|---|---|---|
| KR | 20140063579 | 6/2014 |
| KR | 20150113629 | 10/2015 |
| KR | 20150113631 | 10/2015 |
| KR | 20160097766 | 8/2016 |
| KR | 20150121661 | 10/2016 |
| KR | 20170003234 | 1/2017 |
| KR | 20170038037 | 4/2017 |

* cited by examiner

ORGANIC PHOTODIODE AND ORGANIC IMAGE SENSOR INCLUDING THE SAME

CROSS REFERENCE TO RELATED APPLICATIONS

This application is a 35 U.S.C. § 371 national stage application of PCT International Application No. PCT/KR2018/010895, filed Sep. 17, 2018, which claims priority from Korean Patent Application Nos. 10-2017-0135199 and 10-2018-0110129, filed Oct. 18, 2017 and Sep. 14, 2018, respectively, the contents of which are incorporated herein in their entireties by reference. The above-referenced PCT International Application was published in the Korean language as International Publication No. WO 2019/078491 A1 on Apr. 25, 2019.

TECHNICAL FIELD

This application claims priority to and the benefit of Korean Patent Application Nos. 10-2017-0135199 and 10-2018-0110129 filed in the Korean Intellectual Property Office on Oct. 18, 2017 and Sep. 14, 2018, respectively, the entire contents of which are incorporated herein by reference.

The present specification relates to an organic photodiode and an organic image sensor including the same.

BACKGROUND ART

With the development of smart devices, image sensors including a photodiode are required to have high resolution. However, in the case of a photodiode using silicon which is currently mainly used, it is difficult to decrease the thickness thereof, and there is a limit in increasing the absorbance thereof.

Accordingly, an organic photodiode having high absorbance and various absorption wavelengths has drawn attention as a material replacing a silicon diode, but the existing organic photodiode has a problem in that the efficiency thereof deteriorates in a visible light region as compared to that of the silicon diode. To solve the problem, there is a need for studying organic materials for the organic photodiode.

DETAILED DESCRIPTION OF THE INVENTION

Technical Problem

The present specification provides an organic photodiode and an organic image sensor including the same.

Technical Solution

An exemplary embodiment of the present specification provides an organic photodiode including: a first electrode;
a second electrode provided to face the first electrode; and
an organic material layer having one or more layers provided between the first electrode and the second electrode,
in which one or more layers of the organic material layer include a compound of the following Formula 1.

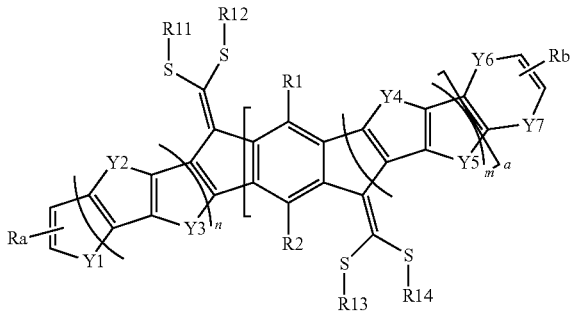

[Formula 1]

In Formula 1,
Ra and Rb are the same as or different from each other, and are each independently a group which serves as an electron acceptor,
Y1 to Y5 are the same as or different from each other, and are each independently CRR', NR, O, SiRR', PR, S, GeRR', Se, or Te,
Y6 and Y7 are different from each other, and are each independently a direct bond, CRR', NR, O, SiRR', PR, S, GeRR', Se, or Te,
a is 0 or 1,
when a is 0, Y6 is a direct bond, and Y7 is CRR', NR, O, SiRR', PR, S, GeRR', Se, or Te,
when a is 1, Y7 is a direct bond, and Y6 is CRR', NR, O, SiRR', PR, S, GeRR', Se, or Te,
n and m are each an integer from 0 to 5,
when n and m are each 2 or more, the structures in the parenthesis are the same as or different from each other,
R11 to R14 are the same as or different from each other, and are each independently an alkyl group having 1 to 4 carbon atoms, and
R1, R2, R, and R' are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heterocyclic group.

Further, an exemplary embodiment of the present specification provides an organic image sensor including the organic photodiode.

Advantageous Effects

An organic photodiode according to an exemplary embodiment of the present specification can absorb light in two or more regions of green, red, and blue regions.

An organic material layer of the organic photodiode according to an exemplary embodiment of the present specification can be formed through a deposition process.

The organic photodiode according to an exemplary embodiment of the present specification has excellent efficiency.

Figure 1:
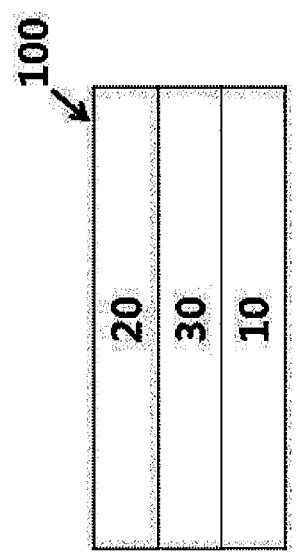
FIG. 1 is a cross-sectional view illustrating an organic photodiode according to an exemplary embodiment of the present specification.

10: First electrode
20: Second electrode
30: Photoactive layer
100: Organic photodiode

BEST MODE

Hereinafter, the present specification will be described in detail.

The present specification provides an organic photodiode including: a first electrode; a second electrode provided to face the first electrode; and an organic material layer having one or more layers provided between the first electrode and the second electrode, in which one or more layers of the organic material layer include the compound of Formula 1.

Sulfur is introduced into an alkyl chain in the compound, so that the crystallinity of the compound is improved due to the intramolecular chalcogen-chalcogen interaction. Further, the compound has a rigid structure due to the introduction of an alkyl group having a small number of carbon atoms into R11 to R14, so that the compound has excellent charge mobility. Accordingly, the compound may exhibit excellent efficiency when applied to an organic photodiode.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

In the present specification,

means a site bonded to another substituent, a monomer, or a binding portion.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxyl group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a siloxane group; a boron group; an amine group; an arylphosphine group; a phosphine oxide group; an aryl group; and a heterocyclic group, or being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked.

In the present specification, a halogen group may be fluorine, chlorine, bromine or iodine.

In the present specification, the alkyl group may be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 2-ethylhexyl, 2-ethylbutyl, 1-methylpentyl, 2-methylpentyl, 4-methyl-2-pentyl, 3,3-dimethylbutyl, heptyl, n-heptyl, 1-methylhexyl, octyl, n-octyl, tert-octyl, 1-methylheptyl, 2-propylpentyl, n-nonyl, 2,2-dimethylheptyl, 1-ethyl-propyl, 1,1-dimethyl-propyl, isohexyl, 4-methylhexyl, 5-methylhexyl, 2,6-dimethyloctane, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

In the present specification, a heterocyclic group includes one or more atoms other than carbon, that is, one or more heteroatoms, and specifically, the heteroatom may include one or more atoms selected from the group consisting of O, N, Se, S, and the like. The number of carbon atoms thereof is not particularly limited, but is preferably 2 to 30, and the heterocyclic group may be monocyclic or polycyclic. Examples of the heterocyclic group include a thiophene group, an imidazolyl group, a thiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a phenothiazinyl group, a dibenzofuranyl group, and the like, but are not limited thereto.

In an exemplary embodiment of the present specification, Formula 1 may be represented by the following Formula 2 or 3.

[Formula 2]

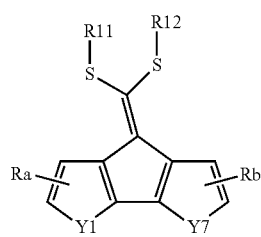

[Formula 3]

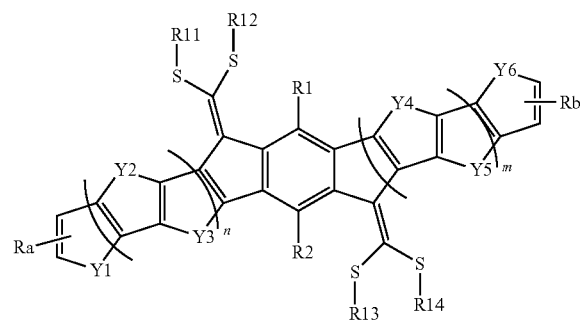

In Formula 2 or 3,

Y6 and Y7 are the same as or different from each other, and are each independently CRR', NR, O, SiRR', PR, S, GeRR', Se, or Te, and Ra, Rb, Y1 to Y5, R1, R2, R11 to R14, n, m, R, and R' are the same as those defined in Formula 1.

In an exemplary embodiment of the present specification, Formula 3 may be represented by the following Formula 1-1 or 1-2.

[Formula 1-1]

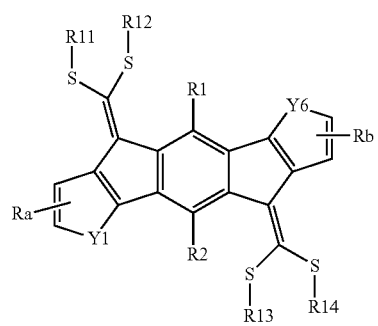

[Formula 1-2]

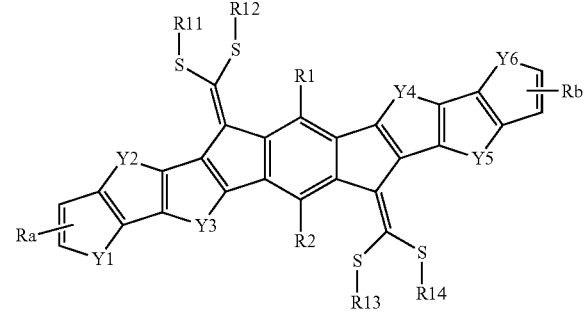

In Formula 1-1 or 1-2,

Y6 is CRR', NR, O, SiRR', PR, S, GeRR', Se, or Te, and

Ra, Rb, Y1 to Y5, R1, R2, R11 to R14, R, and R' are the same as those defined in Formula 1.

In an exemplary embodiment of the present specification, R1 and R2 are hydrogen.

In an exemplary embodiment of the present specification, Ra and Rb are the same as or different from each other, and are each any one of the following structures.

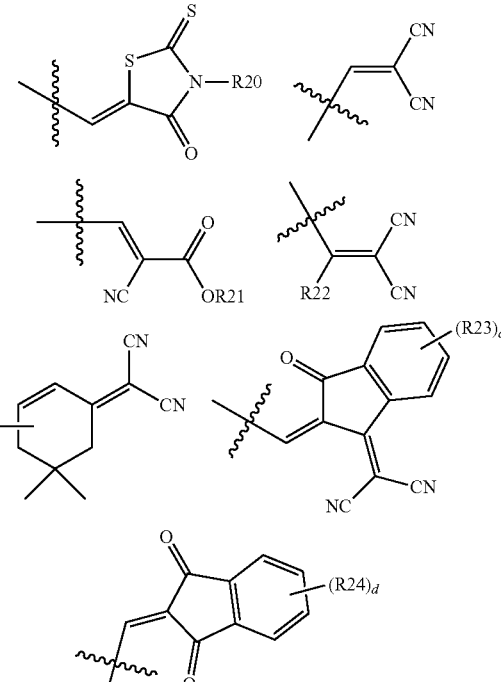

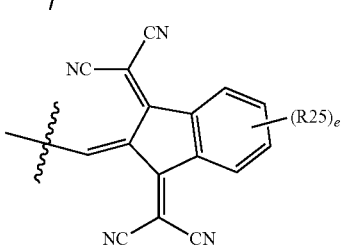

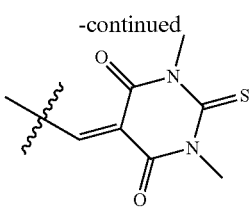

In the structures, c, d, and e are each an integer from 1 to 4, when c, d, and e are each 2 or more, two or more structures in the parenthesis are the same as or different from each other, and R20 to R25 are the same as or different from each other, and are each independently hydrogen; deuterium; a halogen group; a substituted or unsubstituted alkyl group; a substituted or unsubstituted cycloalkyl group; a substituted or unsubstituted aryl group; or a substituted or unsubstituted heterocyclic group.

In an exemplary embodiment of the present specification, Ra and Rb are the same as or different from each other, and are each any one of the following structures.

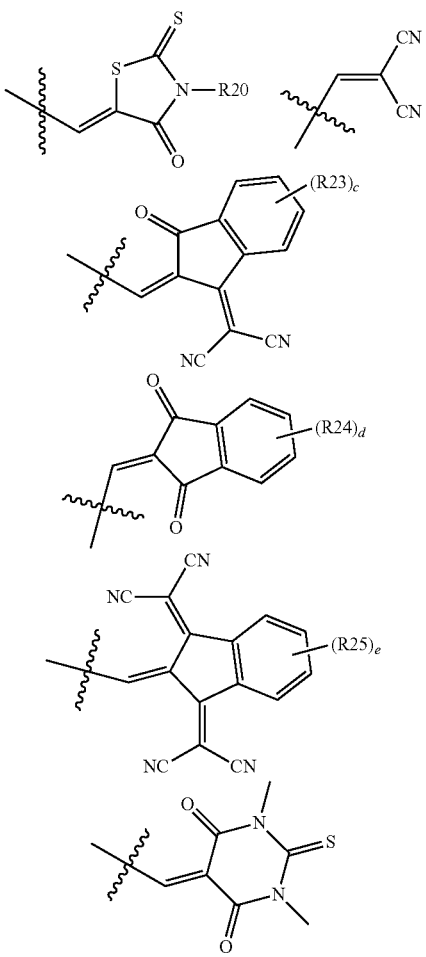

In an exemplary embodiment of the present specification, R20 to R25 are the same as or different from each other, and are each independently hydrogen; deuterium; a halogen group; a substituted or unsubstituted alkyl group; a substituted or unsubstituted cycloalkyl group; a substituted or unsubstituted aryl group; or a substituted or unsubstituted heterocyclic group.

In an exemplary embodiment of the present specification, R20 to R25 are the same as or different from each other, and are each independently hydrogen; or a substituted or unsubstituted alkyl group.

In an exemplary embodiment of the present specification, R20 is a substituted or unsubstituted alkyl group.

In an exemplary embodiment of the present specification, R20 is a substituted or unsubstituted alkyl group having 1 to 30 carbon atoms.

In an exemplary embodiment of the present specification, R20 is a substituted or unsubstituted alkyl group having 1 to 20 carbon atoms.

In an exemplary embodiment of the present specification, R20 is a substituted or unsubstituted alkyl group having 1 to 10 carbon atoms.

In an exemplary embodiment of the present specification, R20 is an ethyl group.

In an exemplary embodiment of the present specification, R21 to R23 are the same as or different from each other, and are each independently hydrogen or a halogen group.

In an exemplary embodiment of the present specification, R21 is hydrogen.

In an exemplary embodiment of the present specification, R22 is hydrogen.

In an exemplary embodiment of the present specification, R23 is hydrogen.

In an exemplary embodiment of the present specification, R23 is fluorine.

In an exemplary embodiment of the present specification, R24 is hydrogen.

In an exemplary embodiment of the present specification, R25 is hydrogen.

In an exemplary embodiment of the present specification, Ra and Rb are the same as or different from each other, and are each any one of the following structures.

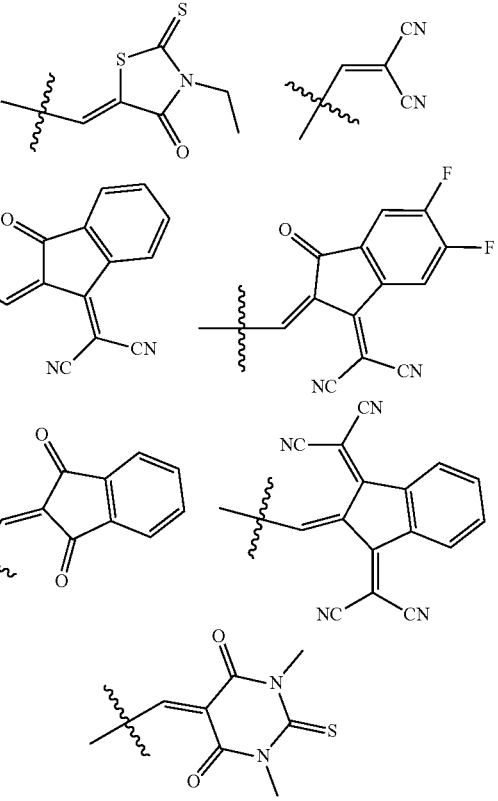

In an exemplary embodiment of the present specification, Formula 1 may be represented by any one of the following Formulae 1-11 to 1-24.
[Formula 1-11]
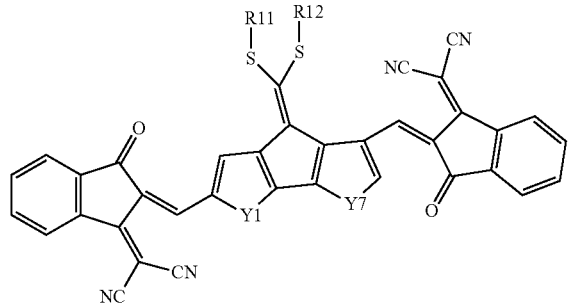
[Formula 1-12]
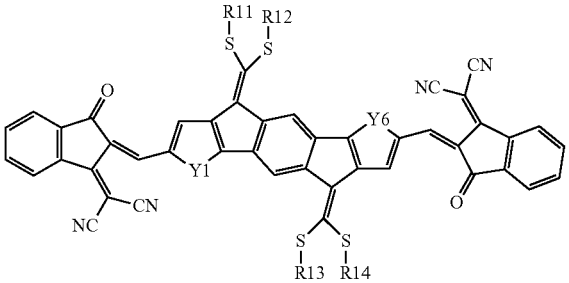
[Formula 1-13]
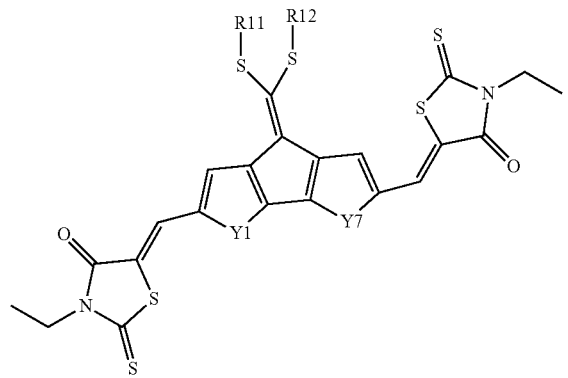
[Formula 1-14]
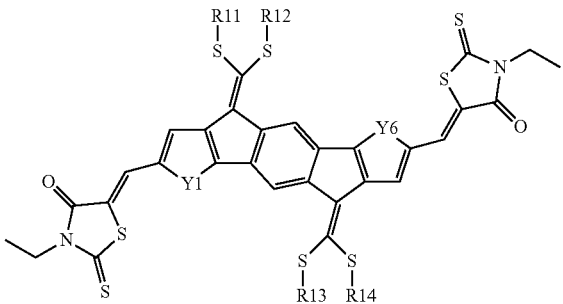
[Formula 1-15]
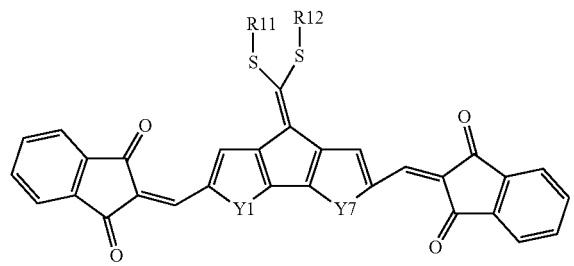
[Formula 1-16]
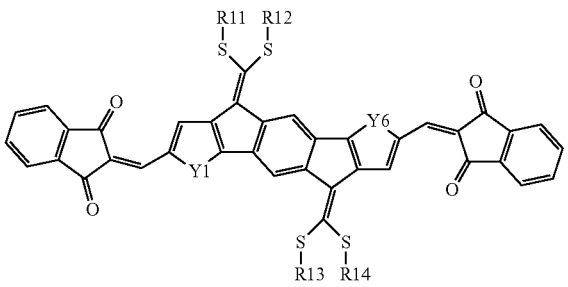
[Formula 1-17]
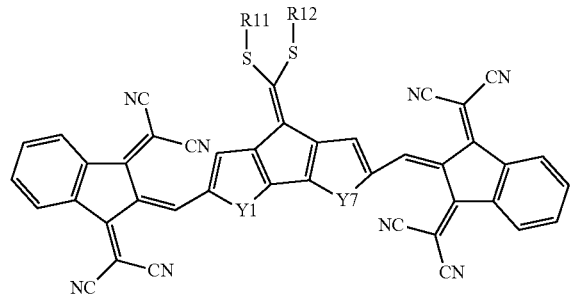
[Formula 1-18]
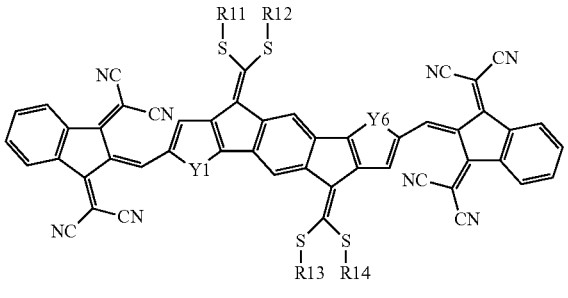

[Formula 1-19]
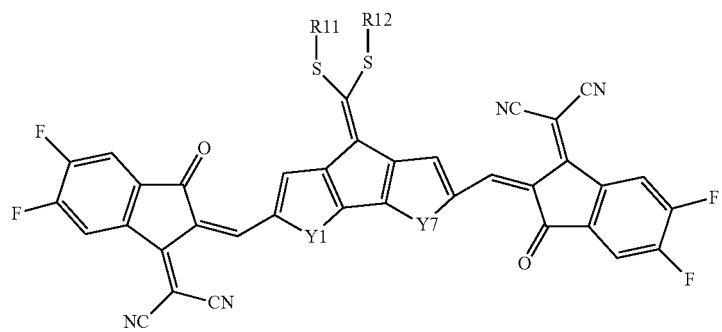
[Formula 1-20]
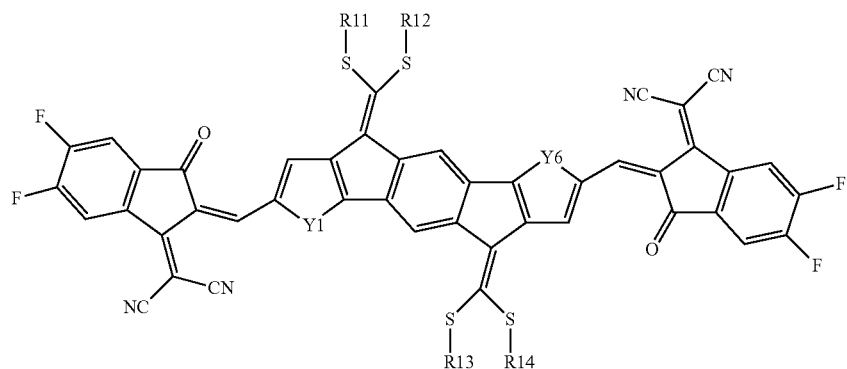
[Formula 1-21]
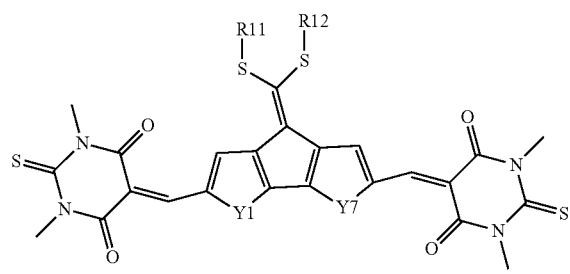
[Formula 1-22]
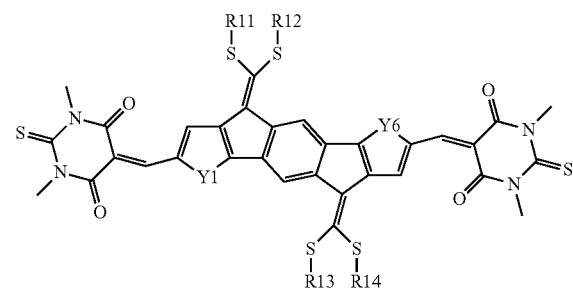
[Formula 1-23]
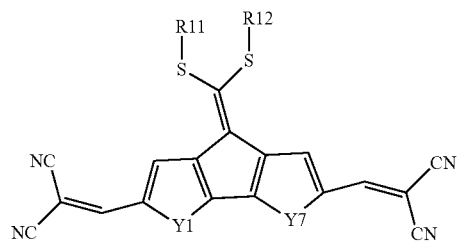
[Formula 1-24]
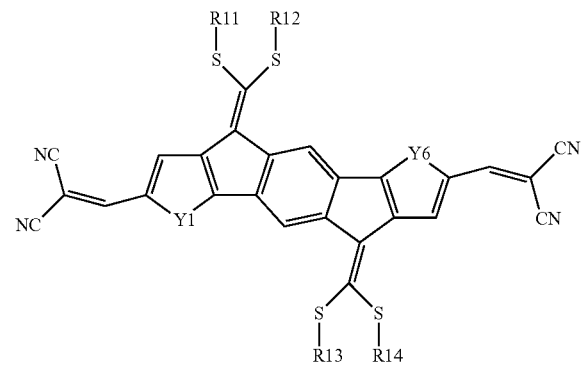

In Formulae 1-11 to 1-24,

Y6 and Y7 are the same as or different from each other, and are each independently CRR', NR, O, SiRR', PR, S, GeRR', Se, or Te, and Y1, R11 to R14, R, and R' are the same as those defined in Formula 1.

In an exemplary embodiment of the present specification, Y1, Y6, and Y7 are each S.

In an exemplary embodiment of the present specification, R11 to R14 are the same as or different from each other, and are each independently an alkyl group having 1 to 4 carbon atoms.

When R11 to R14 have 1 to 4 carbon atoms, the compound has a rigid structure as compared to when R11 to R14 have 5 or more carbon atoms, so that the compound has excellent charge mobility and is advantageous in a deposition process.

In an exemplary embodiment of the present specification, when R11 to R14 have 5 or more carbon atoms, the deposition process cannot be performed.

In an exemplary embodiment of the present specification, R11 to R14 are each a methyl group.

In an exemplary embodiment of the present specification, Formula 1 is represented by any one of the following structures.

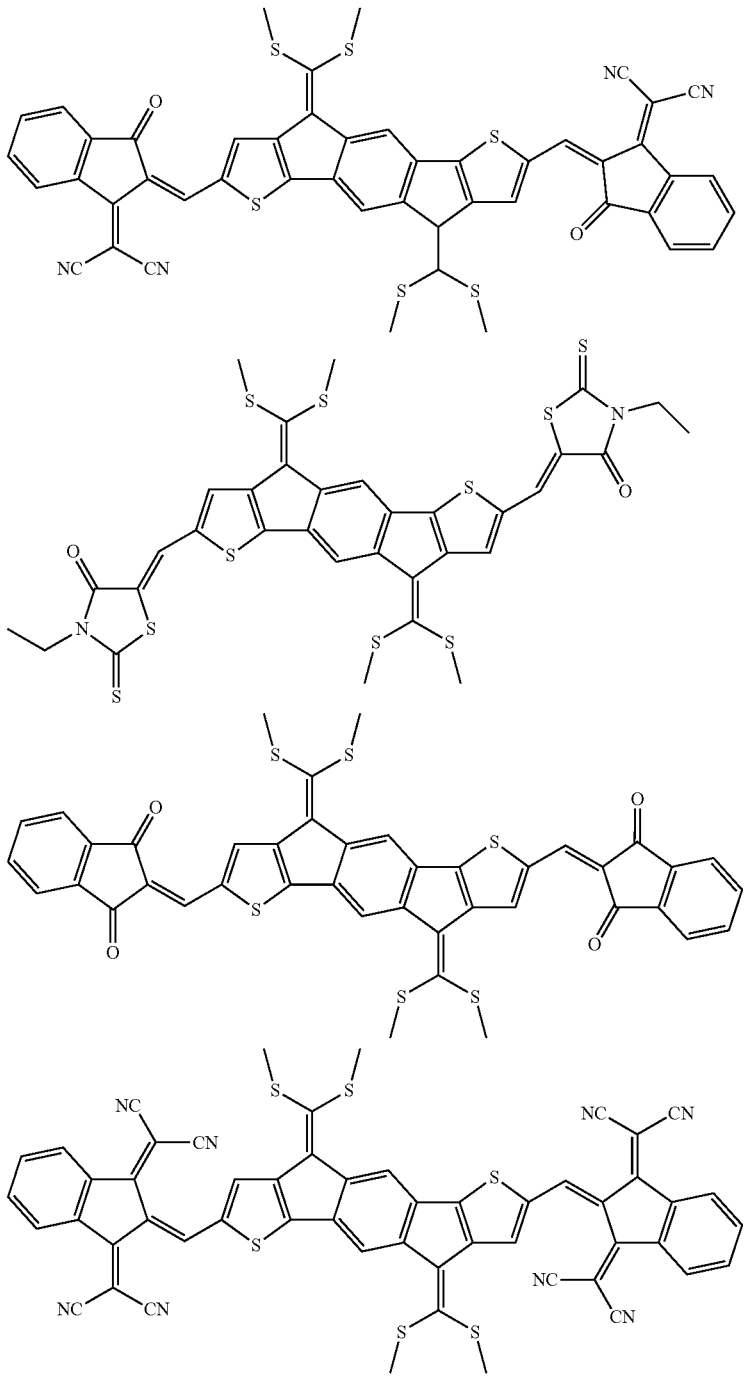

-continued

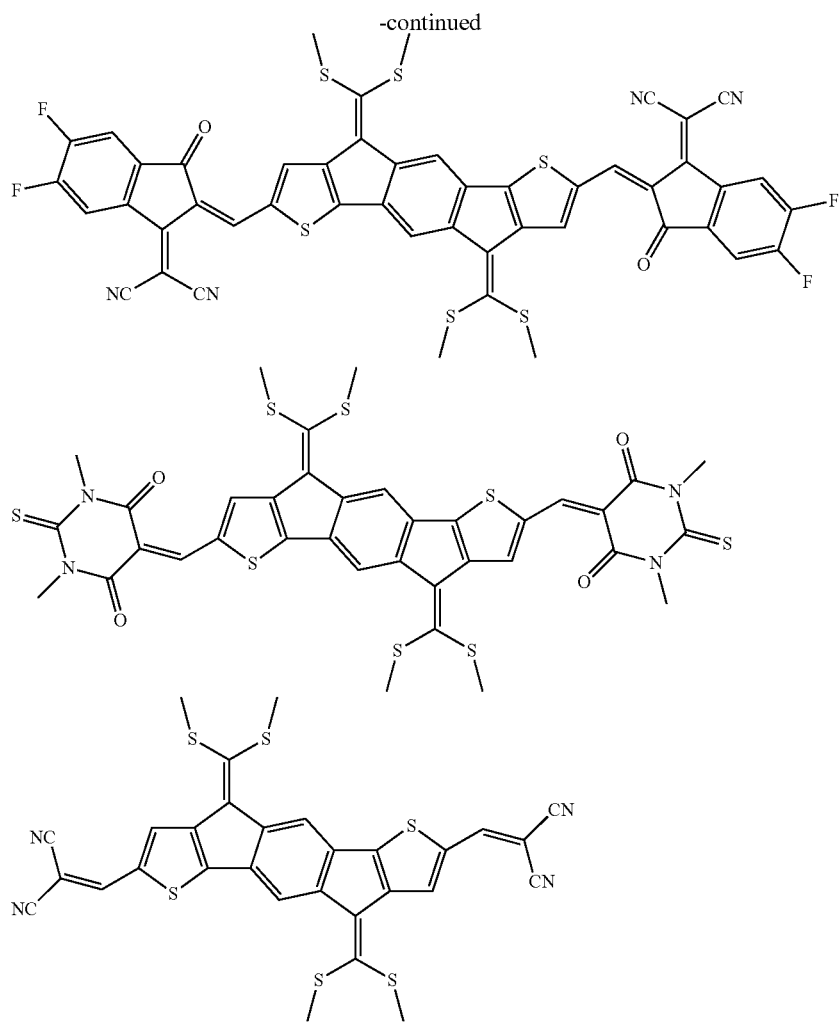

According to an exemplary embodiment of the present specification, the compound has a maximum absorption wavelength at 400 nm to 850 nm. Preferably, the compound has a maximum absorption wavelength at 450 nm to 700 nm. Accordingly, since the compound can absorb light in two or more regions of green, red, and blue regions when applied to a diode, the compound may exhibit an effect in which the efficiency of the device is improved.

In an exemplary embodiment of the present specification, the green region may mean a region whose maximum emission wavelength is present between 500 nm and 570 nm, the red region may mean a region whose maximum emission wavelength is present between 630 nm and 850 nm, and the blue region may mean a region whose maximum emission wavelength is present between 400 nm and 480 nm.

In an exemplary embodiment of the present specification, the compound can absorb light within the entire wavelength range in the visible light region, and can also absorb light in the infrared ray region. For example, the compound can absorb light not only within a wavelength range from 380 nm to 780 nm, but also in a region of 780 nm or more. Accordingly, the compound may exhibit, when applied to a diode, an effect in which the absorption wavelength range of the device is broad.

In an exemplary embodiment of the present specification, the compound may be formed as a film through a deposition process.

In an exemplary embodiment of the present application, the organic photodiode includes: a first electrode; a second electrode provided to face the first electrode; and an organic material layer having one or more layers provided between the first electrode and the second electrode, in which one or more layers of the organic material layer include the compound.

In an exemplary embodiment of the present specification, the organic material layer includes a photoactive layer, the photoactive layer includes an electron donor material and an electron acceptor material, and the electron donor material includes the compound.

In an exemplary embodiment of the present specification, the organic material layer includes a photoactive layer, the photoactive layer includes a p-type organic material layer and an n-type organic material layer, and the p-type organic material layer includes the compound.

In an exemplary embodiment of the present specification, the electron acceptor material and the n-type organic material layer may be selected from the group consisting of fullerene, fullerene derivatives, bathocuproine, semi-conducting elements, semi-conducting compounds, and combinations thereof. Specifically, the electron acceptor material and the n-type organic material layer are one or two or more compounds selected from the group consisting of fullerene, fullerene derivatives ((6,6)-phenyl-$C_{61}$-butyric acid-methy-lester (PCBM) or (6,6)-phenyl-$C_{61}$-butyric acid-cholesteryl ester (PCBCR)), perylene, polybenzimidazole (PBI), and 3,4,9,10-perylene-tetracarboxylic bis-benzimidazole (PTCBI).

In an exemplary embodiment of the present specification, the electron donor material and the electron acceptor material constitute a bulk heterojunction (BHJ). The bulk heterojunction means that an electron donor material and an electron acceptor material are mixed with each other in a photoactive layer.

In an exemplary embodiment of the present specification, the photoactive layer is formed through a deposition process.

In an exemplary embodiment of the present specification, the photoactive layer may be formed by co-depositing an electron donor material and an electron acceptor material. Specifically, the photoactive layer may be formed by putting an electron donor material and an electron acceptor material into each different boat, and simultaneously depositing the materials on an electrode or a charge auxiliary layer.

In an exemplary embodiment of the present specification, an electrode means a first electrode and/or a second electrode, and a charge auxiliary layer means an electron transport layer and/or a hole transport layer.

In an exemplary embodiment of the present specification, the photoactive layer may be formed as a bilayer structure by sequentially depositing an electron donor material and an electron acceptor material. Specifically, the photoactive layer may be formed as a bilayer composed of a p-type organic material layer and an n-type organic material layer by sequentially depositing an electron donor material and an electron acceptor material.

In an exemplary embodiment of the present specification, the p-type organic material layer and the n-type organic material layer may be formed at a thickness ratio of 1:9 to 9:1. More specifically, the p-type organic material layer and the n-type organic material layer may be formed at a thickness ratio of 3:7 to 7:3.

The organic photodiode according to an exemplary embodiment of the present specification includes a first electrode, a photoactive layer, and a second electrode. The organic photodiode may further include a substrate, a hole transport layer, and/or an electron transport layer.

In an exemplary embodiment of the present specification, the organic photodiode may further include a substrate, a hole transport layer, and/or an electron transport layer.

In an exemplary embodiment of the present specification, the organic photodiode may further include an additional organic material layer. The organic photodiode may reduce the number of organic material layers by using an organic material which simultaneously has various functions.

In an exemplary embodiment of the present specification, the first electrode is an anode, and the second electrode is a cathode. In another exemplary embodiment, the first electrode is a cathode, and the second electrode is an anode.

In still another exemplary embodiment, in the organic photodiode, an anode, a hole transport layer, a photoactive layer, an electron transport layer, and a cathode may be arranged in this order, and a cathode, an electron transport layer, a photoactive layer, a hole transport layer, and an anode may also be arranged in this order, but the arrangement order is not limited thereto.

In an exemplary embodiment of the present specification, the organic photodiode has a normal structure. In the normal structure, a substrate, an anode, an organic material layer including a photoactive layer, and a cathode may be stacked in this order. Further, the organic photodiode may additionally include a passivation layer on a cathode.

In an exemplary embodiment of the present specification, the organic photodiode has an inverted structure. In the inverted structure, a substrate, a cathode, an organic material layer including a photoactive layer, and an anode may be stacked in this order. Further, the organic photodiode may additionally include a passivation layer on an anode.

The passivation layer may be formed on an exposed surface of an organic photodiode, may protect an organic photodiode, and may absorb impact, stress, and the like generated when a substrate is removed.

FIG. 1 is a view illustrating an organic photodiode 100 according to an exemplary embodiment of the present specification. According to FIG. 1, in the organic photodiode 100, light is incident from the sides of a first electrode 10 and/or a second electrode 20, so that when an active layer 30 absorbs light in the entire wavelength range, an exciton may be formed inside thereof. The exciton is separated into a hole and an electron in the active layer 30, the separated hole moves to an anode side which is one of the first electrode 10 and the second electrode 20, and the separated electron moves to a cathode side which is the other of the first electrode 10 and the second electrode 20, so that an electric current may flow in the organic photodiode.

In an exemplary embodiment of the present specification, the organic photodiode has a tandem structure.

In an exemplary embodiment of the present specification, in the organic photodiode, materials and/or methods in the art may be used without limitation, except that the compound is used as a photoactive layer.

In an exemplary embodiment of the present specification, the substrate may be a glass substrate or a transparent plastic substrate having excellent transparency, surface smoothness, ease of handling, and water proof properties, but is not limited thereto, and is not limited as long as the substrate is a substrate typically used in an organic electronic device. Specific examples thereof include glass or polyethylene terephthalate (PET), polyethylene naphthalate (PEN), polypropylene (PP), polyimide (PI), triacetyl cellulose (TAC), and the like, but are not limited thereto.

The anode electrode may be made of a material which is transparent and has excellent conductivity, but is not limited thereto. Examples thereof include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide such as $ZnO:Al$ or $SnO_2:Sb$; a conductive polymer such as poly(3-methylthiophene), poly[3,4-(ethylene-1,2-dioxy)thiophene] (PEDOT), polypyrrole, and polyaniline; and the like, but are not limited thereto.

A method of forming the anode electrode is not particularly limited, but the anode electrode may be formed, for example, by being applied onto one surface of a substrate or coated in the form of a film using a method such as sputtering, e-beam, thermal deposition, spin coating, screen printing, inkjet printing, doctor blade, or gravure printing.

When the anode electrode is formed on a substrate, the anode electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a hot plate at 100° C. to 150° C. for 1 to 30 minutes, preferably at 120° C. for 10 minutes in order to remove moisture, and when the substrate is completely cleaned, modify the surface of the substrate to be hydrophilic.

Through the surface modification as described above, the junction surface potential may be maintained at a level suitable for a surface potential of a photoactive layer. Further, during the modification, a polymer thin film may be easily formed on an anode electrode, and the quality of the thin film may also be improved.

Examples of a pre-treatment technology for an anode electrode include a) a surface oxidation method using a parallel flat plate-type discharge, b) a method of oxidizing a surface through ozone produced by using UV rays in a vacuum state, c) an oxidation method using oxygen radicals produced by plasma, and the like.

One of the methods may be selected depending on the state of the anode electrode or the substrate. However, in all the methods, it is preferred to prevent oxygen from being separated from the surface of the anode electrode or the substrate, and maximally inhibit moisture and organic materials from remaining. In this case, it is possible to maximize a substantial effect of the pre-treatment.

As a specific example, it is possible to use a method of oxidizing the surface through ozone produced by using UV. In this case, a patterned ITO substrate after being ultrasonically cleaned is baked on a hot plate and dried well, and then introduced into a chamber, and the patterned ITO substrate may be cleaned by ozone generated by allowing an oxygen gas to react with UV light by operating a UV lamp.

However, the surface modification method of the patterned ITO substrate in the present specification need not be particularly limited, and any method may be used as long as the method is a method of oxidizing a substrate.

The cathode electrode may be made of a metal having a low work function, but is not limited thereto. Specific examples thereof include: a metal such as magnesium, calcium, sodium, potassium, titanium, indium, yttrium, lithium, gadolinium, aluminum, silver, tin, and lead, or an alloy thereof; or a multi-layer structured material such as LiF/Al, LiO$_2$/Al, LiF/Fe, Al:Li, Al:BaF$_2$, and Al:BaF$_2$:Ba, but are not limited thereto.

The cathode electrode may be deposited and formed in a thermal evaporator showing a vacuum degree of 5×10$^{-7}$ torr or less, but the forming method is not limited to this method.

The passivation layer may be composed of an inorganic-based material such as a silicon oxide film (SiOx) and a silicon nitride film (SiNx), or an organic-based material such as benzocyclobutene (BCB) and photo acryl, but the material is not limited thereto.

The passivation layer may be formed by using a plasma enhanced chemical vapor deposition (PECVD) method on an exposed surface of an organic photodiode.

A material for the hole transport layer and/or a material for the electron transport layer serve to efficiently transfer electrons and holes separated from a photoactive layer to an electrode, and the materials are not particularly limited.

Examples of the material for the hole transport layer include: poly(3,4-ethylenedioxythiophene) doped with poly(styrenesulfonic acid) (PEDOT:PSS); molybdenum oxide (MoO$_x$); vanadium oxide (V$_2$O$_5$); nickel oxide (NiO); tungsten oxide (WO$_x$); and the like, but are not limited thereto.

The material for the electron transport layer may be bathocuproine (BCP) or electron-extracting metal oxides, and specific examples thereof include: bathocuproine (BCP); metal complexes of 8-hydroxyquinoline; complexes including Alq$_3$; metal complexes including Liq; LiF; Ca; titanium oxide (TiO$_x$); zinc oxide (ZnO); cesium carbonate (Cs$_2$CO$_3$); and the like, but are not limited thereto.

The hole transport layer and the electron transport layer may be formed from each material by a method used in the art. For example, after each material is dissolved in an organic solvent, the hole transport layer and the electron transport layer may be formed from the resulting solution by using a method such as spin coating, dip coating, screen printing, spray coating, doctor blade, and brush painting, and the compound is produced in the form of a film through a deposition process, but the method is not limited to these methods.

An exemplary embodiment of the present specification provides an organic image sensor including the organic photodiode.

The organic image sensor according to an exemplary embodiment of the present specification may be applied to an electronic device, and may be applied to, for example, a mobile phone, a digital camera, and the like, but the application range is not limited thereto.

MODE FOR INVENTION

The method for producing the compound, the method for manufacturing an organic photodiode including the same, and the production of an organic image sensor including the same will be specifically described in the following Preparation Examples and Examples. However, the following Examples are provided for exemplifying the present specification, and the scope of the present specification is not limited thereby.

Preparation Example 1. Production of Compound A-3

(1) Production of Compound A-2

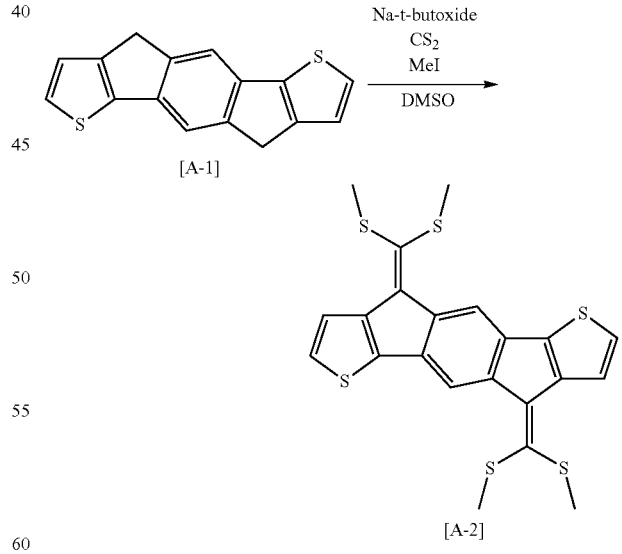

Compound A-1 (4 g, 15.02 mmol) and 6.56 g (68.3 mmol) of sodium tert-butoxide (Na-t-butoxide) were added to 100 mL of dry dimethyl sulfoxide (dry DMSO) at room temperature. After 20 minutes, carbon disulfide (CS$_2$) was slowly injected thereinto by using a syringe. After 30 minutes, methyl iodide (MeI) was added thereto by using a syringe, and the mixture was stirred at room temperature for 10 hours. And then, the product was poured into iced water, and the remaining MeI was quenched by adding NH₄OH thereto. After the produced precipitate was extracted with diethyl ether, the product was washed three times with water. And then, the organic layer was purified with column chromatography to obtain Compound A-2.

Figure 2:
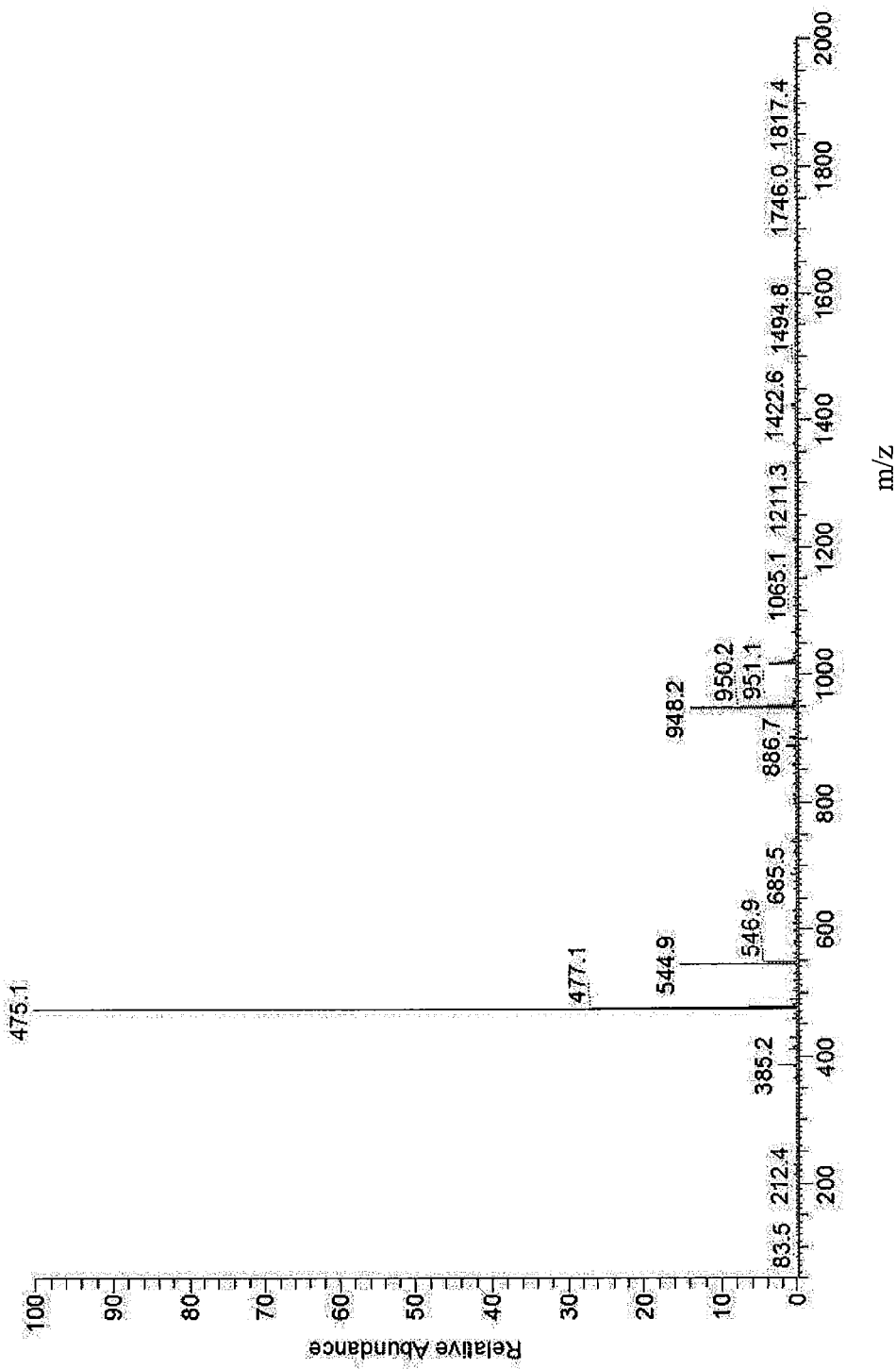
FIG. 2 is a view illustrating an MS spectrum of Compound A-2.

FIG. 2 is a view illustrating an MS spectrum of Compound A-2.

(2) Production of Compound A-3

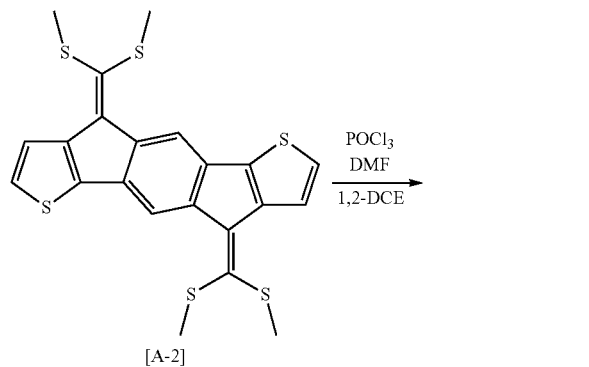

[A-2]

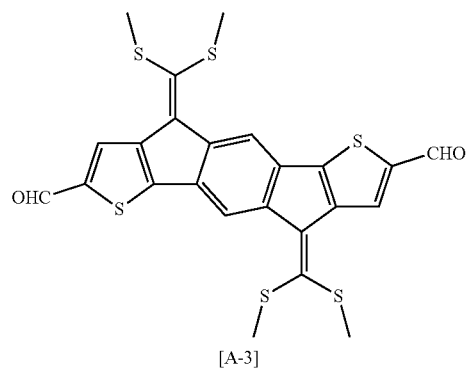

[A-3]

6.22 mL of phosphorus oxychloride (POCl₃)(66.72 mmol) was added to 5.42 mL of N,N-dimethylformamide (DMF) (70 mmol), and the resulting mixture was stirred at 0° C. for 60 minutes to prepare a mixed solution. A solution, in which 3.95 g (8.34 mmol) of Compound A-2 was dissolved in 120 mL of dichloroethane (DCE), was added to the prepared mixed solution, and the resulting mixture was stirred at 100° C. for 48 hours. After the stirring, 1 M acetate was added thereto, and the resulting mixture was stirred for 1 hour for neutralization. Thereafter, the product was extracted with dichloromethane, and the extract was dried over anhydrous magnesium sulfate (MgSO₄) and evaporated. After the solvent was removed under reduced pressure, the residue was purified through flash chromatography (hexane:chloroform=4:1) using hexane and chloroform as an eluent to obtain Compound A-3.

Preparation Example 2. Production of Compound 1

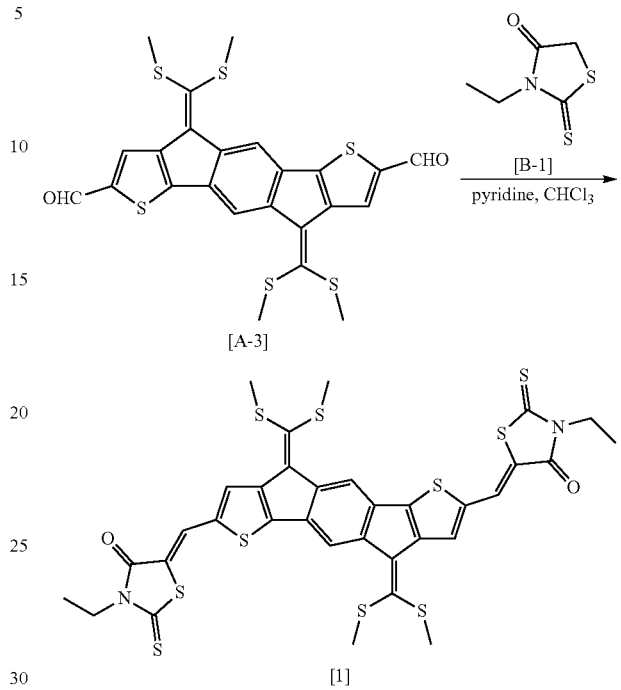

Compound A-3 (0.212 g, 0.4 mmol) and Compound B-1 (0.645 g, 4.0 mmol) were dissolved in 50 mL of chloroform (CHCl₃), and 3 mL of pyridine was slowly injected thereinto at room temperature. Thereafter, after the mixture was refluxed for 24 hours, the temperature was lowered to room temperature, and then the precipitate was filtered. The filtered portion was stirred again in heated chloroform for 2 hours, and then filtered again to obtain Compound 1. In this case, it was confirmed by measuring the molecular weight using MALDI-TOF that Compound 1 was produced (MALDI-TOF molecular weight: 815.8 m/z).

Figure 3:
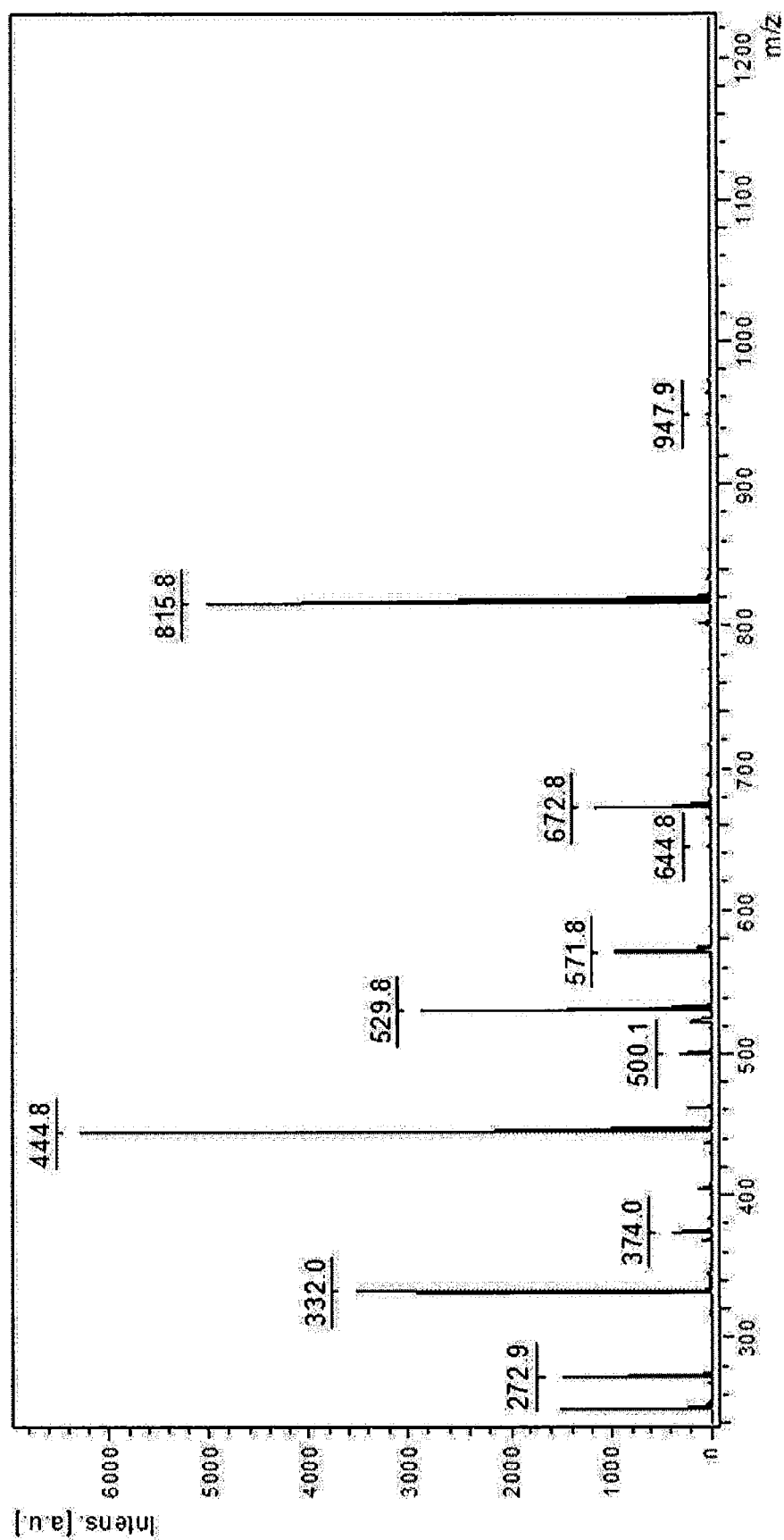
FIG. 3 is a view illustrating a MALDI-TOF measurement result of Compound 1.

FIG. 3 is a view illustrating a MALDI-TOF measurement result of Compound 1.

Preparation Example 3. Production of Compound 2

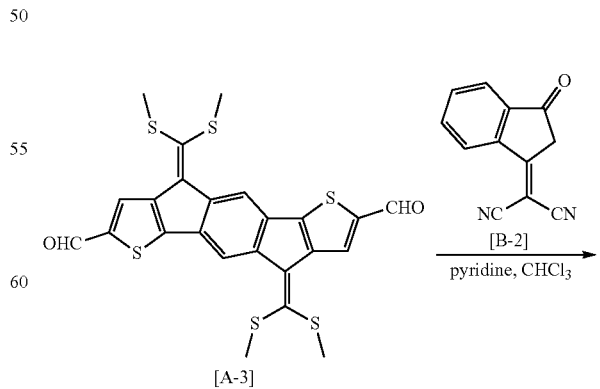

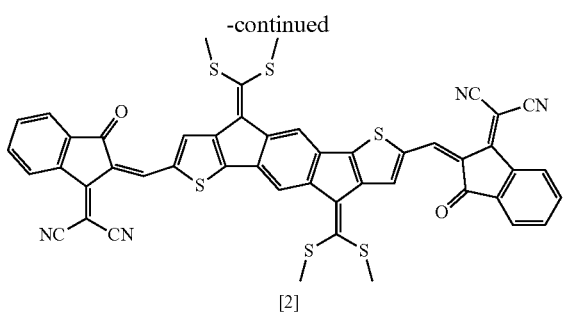

[2]

Compound 2 was produced in the same manner as in Preparation Example 2, except that Compound B-2 was used instead of Compound B-1. In this case, it was confirmed by measuring the molecular weight using MALDI-TOF that Compound 2 was produced (MALDI-TOF molecular weight: 882.3 m/z).

Preparation Example 4. Production of Compound 3

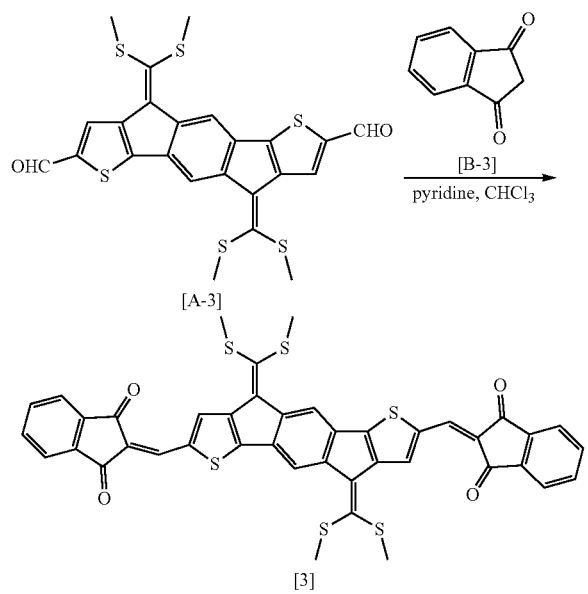

[3]

Compound 3 was produced in the same manner as in Preparation Example 2, except that Compound B-3 was used instead of Compound B-1. In this case, it was confirmed by measuring the molecular weight using MALDI-TOF that Compound 3 was produced (MALDI-TOF molecular weight: 786.5 m/z).

Preparation Example 5. Production of Compound 4

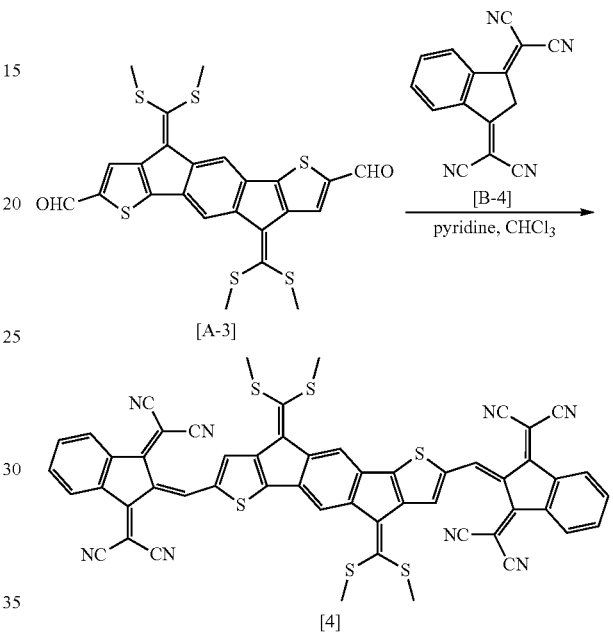

[4]

Compound 4 was produced in the same manner as in Preparation Example 2, except that Compound B-4 was used instead of Compound B-1. In this case, it was confirmed by measuring the molecular weight using MALDI-TOF that Compound 4 was produced (MALDI-TOF molecular weight: 978.3 m/z).

Preparation Example 6. Production of Compound 5

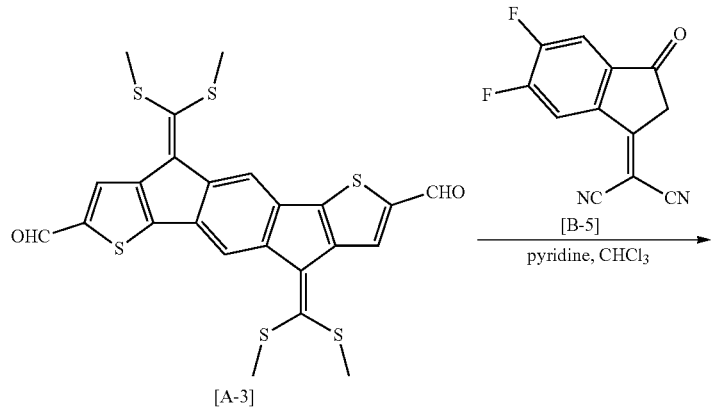

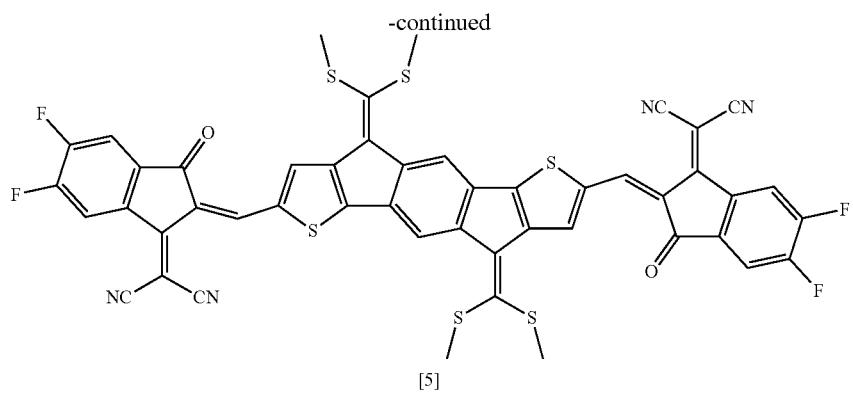

[5]

Compound 5 was produced in the same manner as in Preparation Example 2, except that Compound B-5 was used instead of Compound B-1. In this case, it was confirmed by measuring the molecular weight using MALDI-TOF that Compound 5 was produced (MALDI-TOF molecular weight: 954.1 m/z).

Preparation Example 7. Production of Compound 6

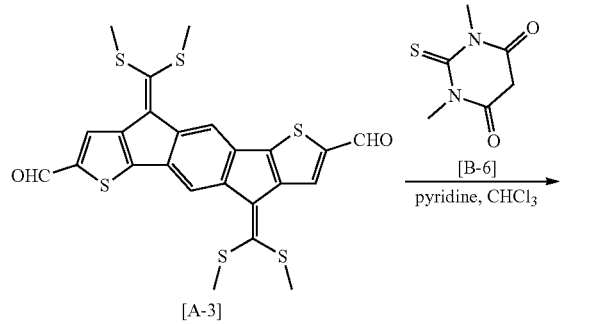

[A-3]

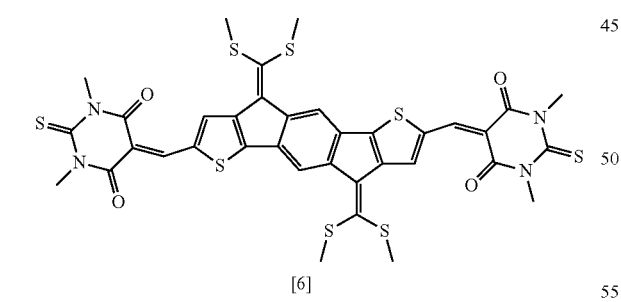

[6]

Compound 6 was produced in the same manner as in Preparation Example 2, except that Compound B-6 was used instead of Compound B-1. In this case, it was confirmed by measuring the molecular weight using MALDI-TOF that Compound 6 was produced (MALDI-TOF molecular weight: 838.1 m/z).

Preparation Example 8. Production of Compound 7

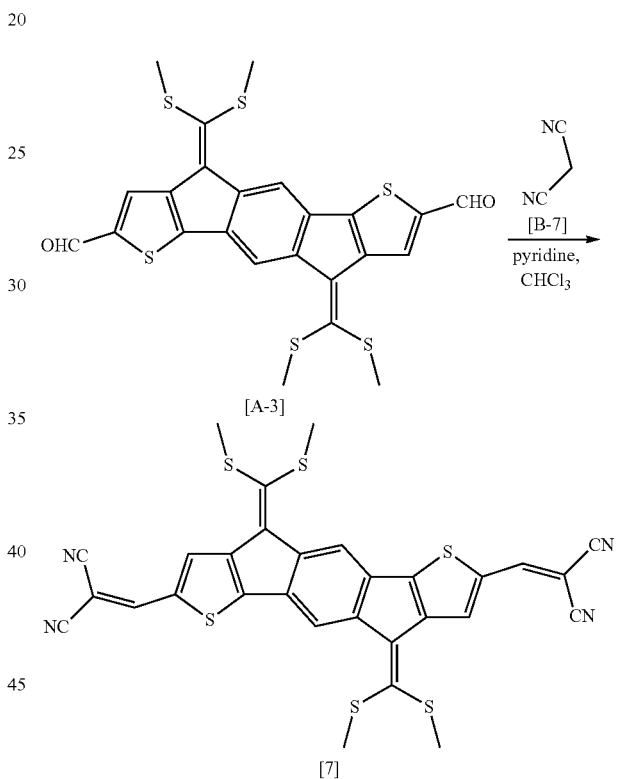

[7]

Compound 7 was produced in the same manner as in Preparation Example 2, except that Compound B-7 was used instead of Compound B-1. In this case, it was confirmed by measuring the molecular weight using MALDI-TOF that Compound 7 was produced (MALDI-TOF molecular weight: 625.8 m/z).

Example 1

A first electrode (an anode) having a thickness of about 100 nm was formed by stacking ITO on a glass substrate by sputtering, and a molybdenum oxide (MoOx, $0<x\leq3$) thin film as a hole transport layer was stacked to a thickness of 30 nm thereon. Next, a photoactive layer having a thickness of 80 nm was formed by depositing the compound in the Preparation Example (a p-type organic material layer) and $C_{60}$ (an n-type organic material layer) at a thickness ratio of 3:4 on the molybdenum oxide (MoOx, 0<x≤3) thin film. Next, an electron transport layer was formed by thermally depositing bathocuproine (BCP) to a thickness of 8 nm on the photoactive layer. Finally, a second electrode (a cathode) having a thickness of 80 nm was formed by thermally depositing aluminum (Al), thereby manufacturing an organic photoelectric device.

Comparative Example 1

An attempt to manufacture an organic photoelectric device was made by using Compound A-2, but a film could not be formed from Compound A-2 which was in a viscous state, and as a result, the organic photoelectric device could not be manufactured.

Comparative Example 2

After a compound with R11 to R14 having 5 or more carbon atoms was synthesized in Formula 1, an attempt to manufacture an organic photoelectric device was made, but a deposition process could not be performed.

The performances of the organic photoelectric devices manufactured in Examples 1 to 5 were measured and are shown in Table 1.

TABLE 1

|  | $J$ (A/cm$^2$) at 0 mW/cm$^2$, −1 V | $J$ (A/cm$^2$) at 100 mW/cm$^2$, −1 V | $J$ (A/cm$^2$) at 0 mW/cm$^2$, −3 V | $J$ (A/cm$^2$) at 100 mW/cm$^2$, −3 V |
| --- | --- | --- | --- | --- |
| Example 1 | 4.98E−8 | 4.03E−03 | 3.97E−7 | 4.96E−03 |
| Example 2 | 2.58E−8 | 5.19E−03 | 8.25E−7 | 9.15E−03 |
| Example 3 | 8.65E−8 | 5.29E−03 | 5.73E−7 | 8.25E−03 |
| Example 4 | 5.19E−8 | 3.21E−03 | 4.76E−7 | 5.38E−03 |
| Example 5 | 7.28E−8 | 2.49E−03 | 9.64E−7 | 6.11E−03 |

Through the results from Table 1, it can be confirmed that in the organic photoelectric devices manufactured in the Examples, a current (J) value exhibits a value close to 0 under the no light condition (0 mW/cm$^2$), and the current value is increased under the light condition (100 mW/cm$^2$). That is, it can be confirmed that a case where the compound according to an exemplary embodiment of the present specification is applied to the organic photoelectric device exhibits an excellent performance.

Figure 4:
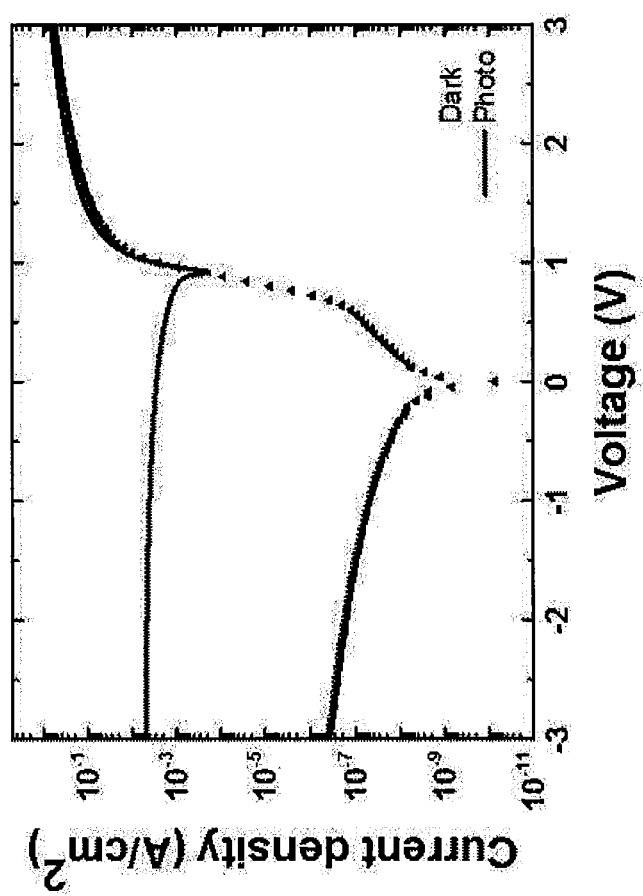
FIG. 4 is a view illustrating the current density according to the voltage in an organic photoelectric device manufactured in Example 1.

FIG. 4 is a view illustrating the current density according to the voltage in an organic photoelectric device manufactured in Example 1. Specifically, in FIG. 4, $J_{dark}$ are data obtained by measuring a current density according to the voltage in a no light state, and $J_{photo}$ are data obtained by measuring a current density according to the voltage while light with 100 mW/cm$^2$ is irradiated. The closer to 0 the current density according to the voltage is in a no light state and the higher the current density according to the voltage is in a light state, the better the performance is. As a result of measuring the performance of Example 1, the current value when light is not present ($J_{dark}$) exhibits a value close to 0, and as a result, it can be confirmed that the performance of the device is excellent.

What is claimed is:
1. An organic photodiode comprising:
a first electrode;
a second electrode facing the first electrode; and
an organic material layer comprising one or more layers between the first electrode and the second electrode, wherein the one or more layers of the organic material layer comprise a compound of Formula 1:

[Formula 1]

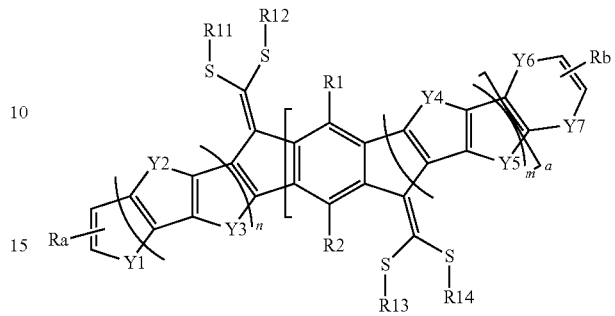

wherein:
Ra and Rb are the same as or different from each other, and are each independently a group which serves as an electron acceptor;
Y1 to Y5 are the same as or different from each other, and are each independently CRR', NR, O, SiRR', PR, S, GeRR', Se, or Te;
Y6 and Y7 are different from each other, and are each independently a direct bond, CRR', NR, O, SiRR', PR, S, GeRR', Se, or Te;
a is 0 or 1;
when a is 0, Y6 is a direct bond, and Y7 is CRR', NR, O, SiRR', PR, S, GeRR', Se, or Te;
when a is 1, Y7 is a direct bond, and Y6 is CRR', NR, O, SiRR', PR, S, GeRR', Se, or Te;
n and m are each an integer from 0 to 5;
when n and m are each 2 or more, structures in parenthesis are the same as or different from each other;
R11 to R14 are the same as or different from each other, and are each independently an alkyl group having 1 to 4 carbon atoms; and
R1, R2, R, and R' are the same as or different from each other, and are each independently hydrogen, deuterium, a substituted or unsubstituted alkyl group, a substituted or unsubstituted cycloalkyl group, a substituted or unsubstituted aryl group, or a substituted or unsubstituted heterocyclic group.

2. The organic photodiode of claim 1, wherein the compound of Formula 1 is a compound of Formula 3:

[Formula 3]

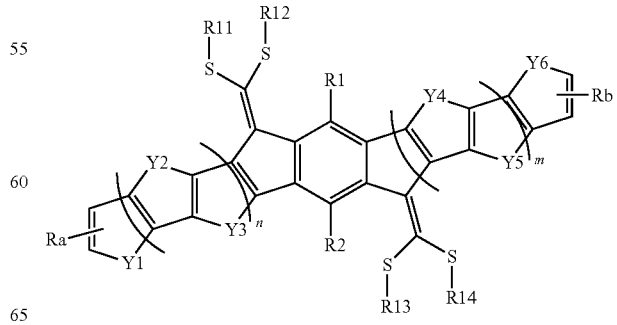

wherein:
Y6 is CRR', NR, O, SiRR', PR, S, GeRR', Se, or Te; and
Ra, Rb, Y1 to Y5, R1, R2, R11 to R14, n, m, R, and R' are the same as those defined in Formula 1.

3. The organic photodiode of claim 2, wherein the compound of Formula 3 is a compound of Formula 1-1 or Formula 1-2:

[Formula 1-1]

[Formula 1-2]

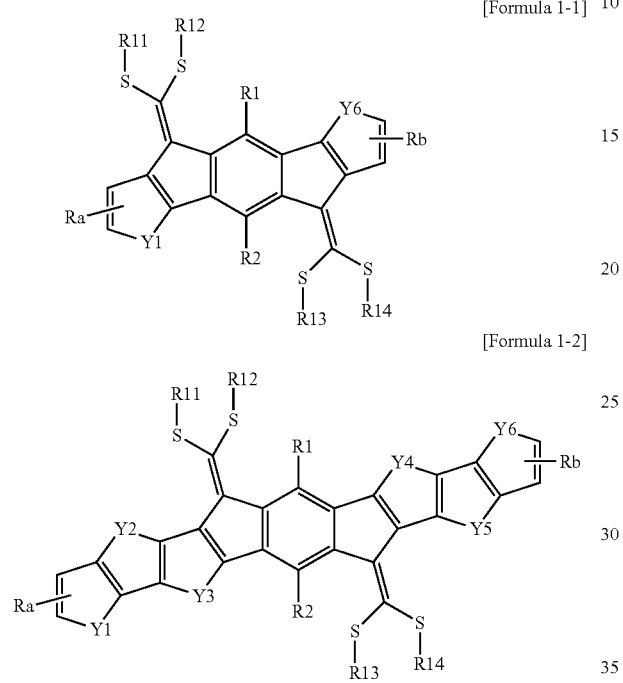

wherein:
Y6 is CRR', NR, O, SiRR', PR, S, GeRR', Se, or Te; and
Ra, Rb, Y1 to Y5, R1, R2, R11 to R14, R, and R' are the same as those defined in Formula 1.

4. The organic photodiode of claim 1, wherein Ra and Rb are the same as or different from each other, and are each any one of the following structures:

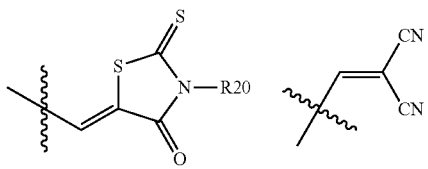

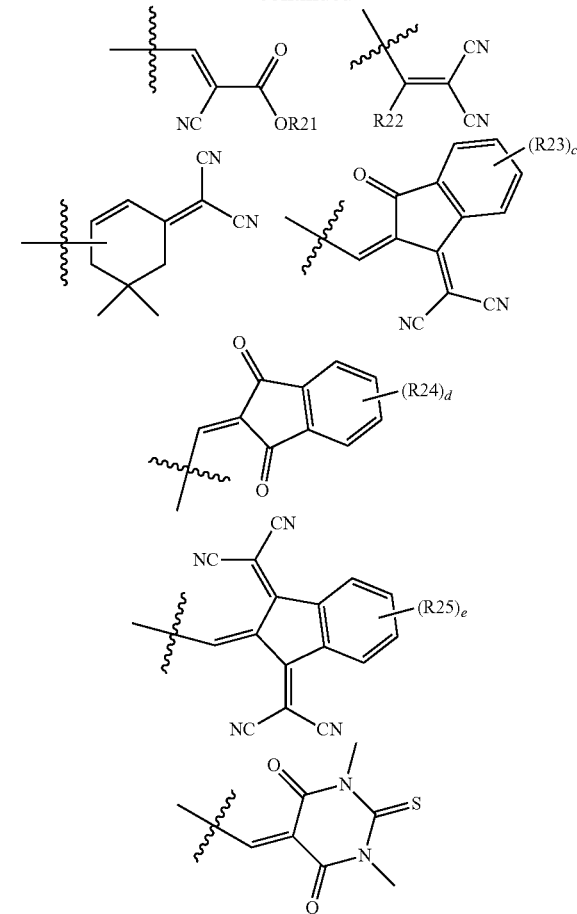

wherein:
c, d, and e are each an integer from 1 to 4;
when c, d, and e are each 2 or more, two or more structures in the parenthesis are the same as or different from each other; and
R20 to R25 are the same as or different from each other, and are each independently hydrogen, deuterium, a halogen group, a substituted or unsubstituted alkyl group, a substituted or unsubstituted cycloalkyl group, a substituted or unsubstituted aryl group, or a substituted or unsubstituted heterocyclic group.

5. The organic photodiode of claim 1, wherein R1 and R2 are each hydrogen.

6. The organic photodiode of claim 1, wherein the compound of Formula 1 is a compound of any one of Formulae 1-12, 1-14, 1-16, 1-18, 1-20, 1-22, and 1-24:

[Formula 1-12]

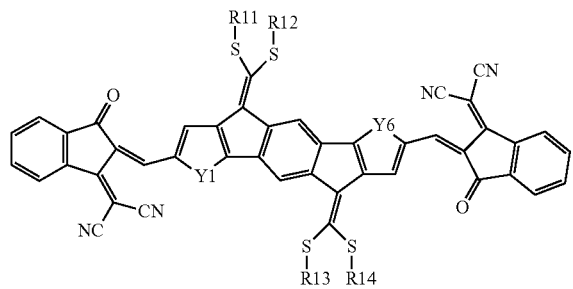

[Formula 1-14]

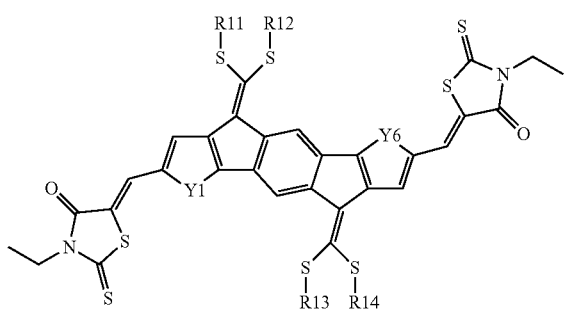

-continued
[Formula 1-16]
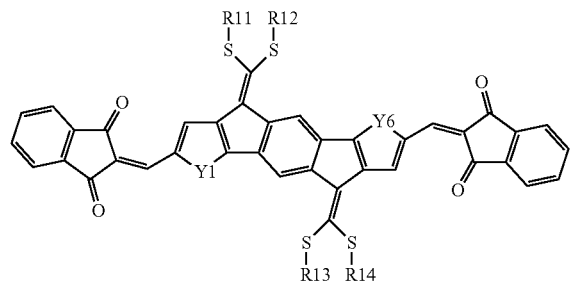
[Formula 1-18]
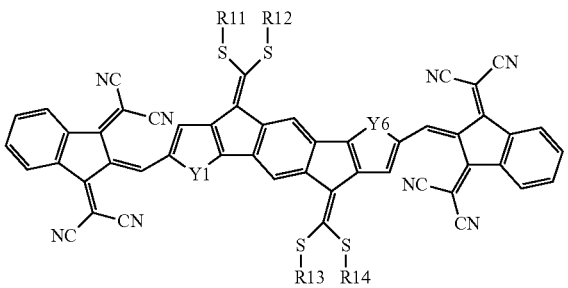
[Formula 1-20]
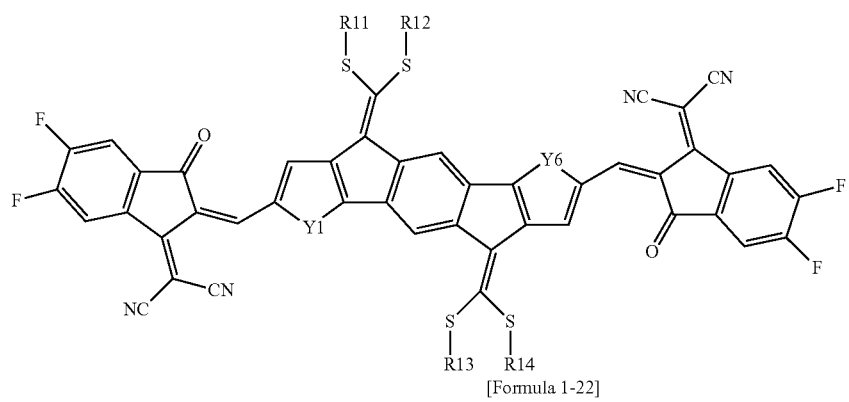
[Formula 1-22]
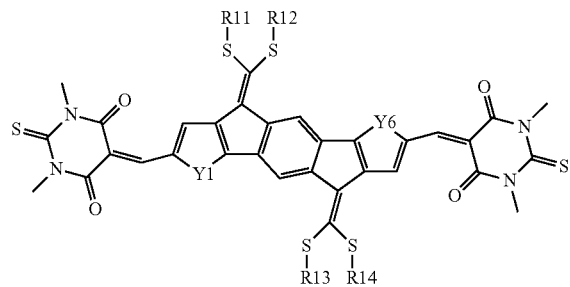
[Formula 1-24]
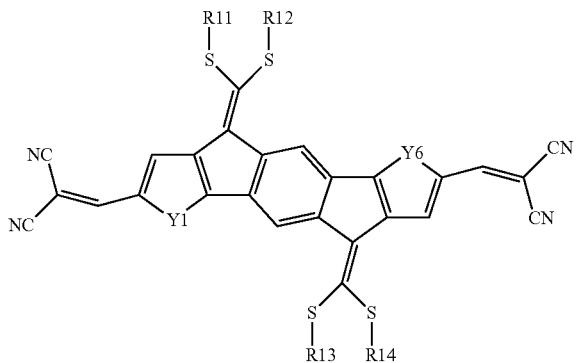
wherein:
Y6 is CRR', NR, O, SiRR', PR, S, GeRR', Se, or Te; and
Y1, R11 to R14, R, and R' are the same as those defined in Formula 1.
7. The organic photodiode of claim 1, wherein Y1 to Y5 are each S.
8. The organic photodiode of claim 1, wherein the compound of Formula 1 is any one of the following structures:
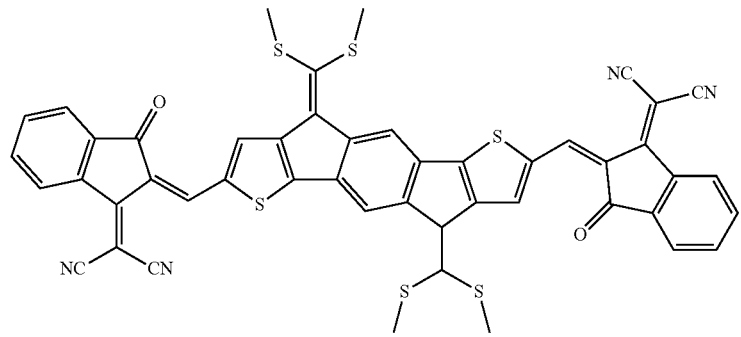

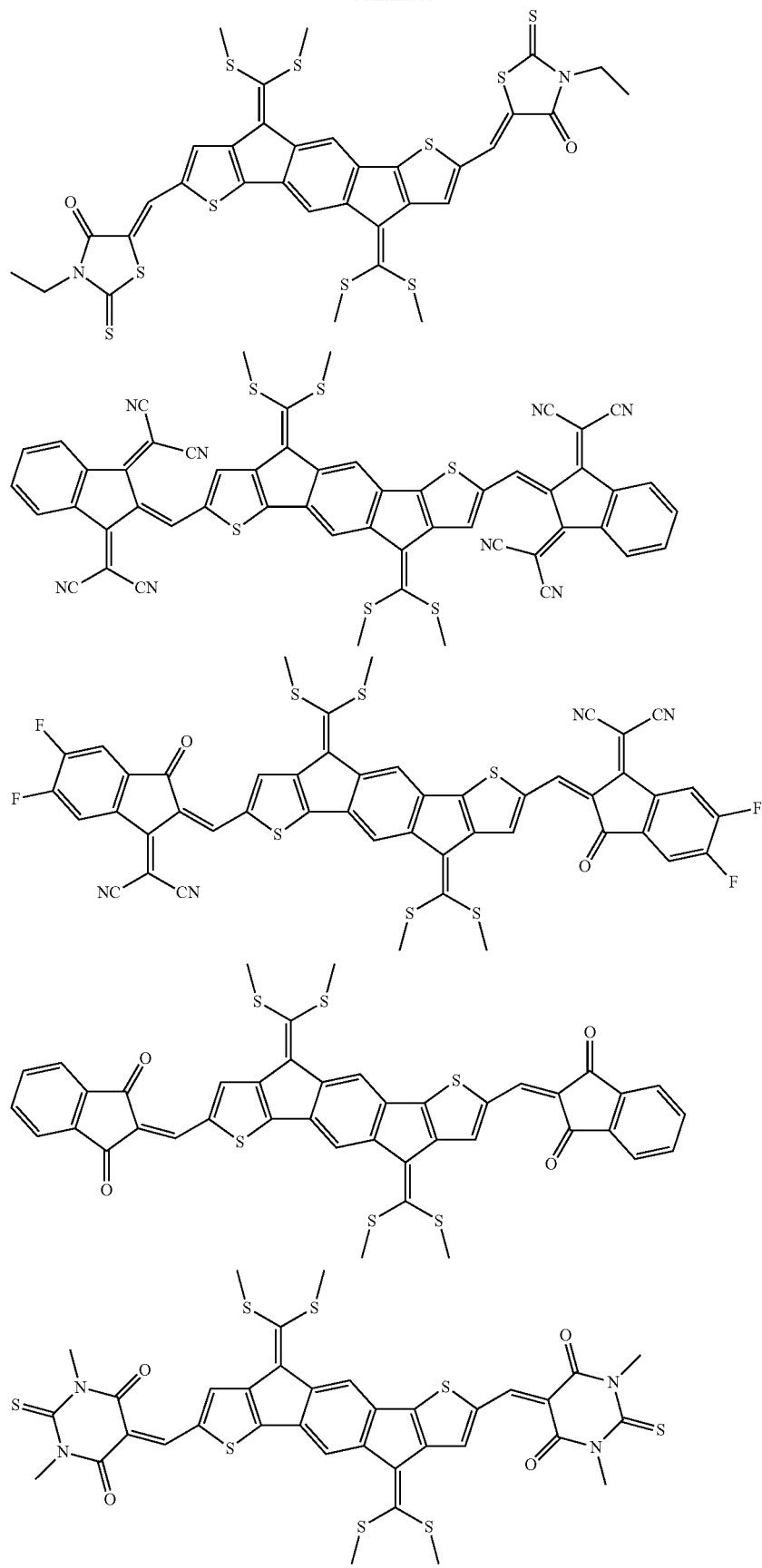

-continued

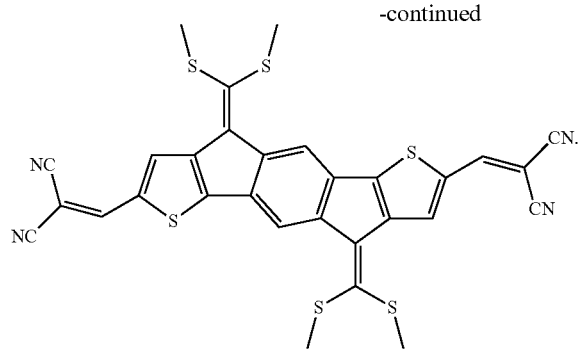

9. The organic photodiode of claim 1, wherein the organic material layer comprises a photoactive layer,
the photoactive layer comprises an electron donor material and an electron acceptor material, and
the electron donor material comprises the compound of Formula 1.

10. The organic photodiode of claim 1, wherein the organic material layer comprises a photoactive layer,
the photoactive layer comprises a p-type organic material layer and an n-type organic material layer, and
the p-type organic material layer comprises the compound of Formula 1.

11. An organic image sensor comprising the organic photodiode according to claim 1.

12. The organic photodiode of claim 1, wherein the compound of Formula 1 is a compound of Formula 2:

[Formula 2]

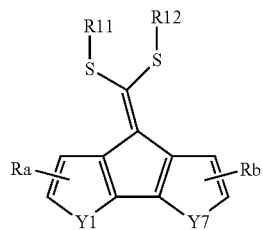

wherein:
Y7 is CRR', NR, O, SiRR', PR, S, GeRR', Se, or Te; and
Ra, Rb, Y1, R11, R12, R, and R' are the same as those defined in Formula 1.

13. The organic photodiode of claim 1, wherein the compound of Formula 1 is a compound of any one of Formulae 1-11, 1-13, 1-15, 1-17, 1-19, 1-21, and 1-23:

[Formula 1-11]

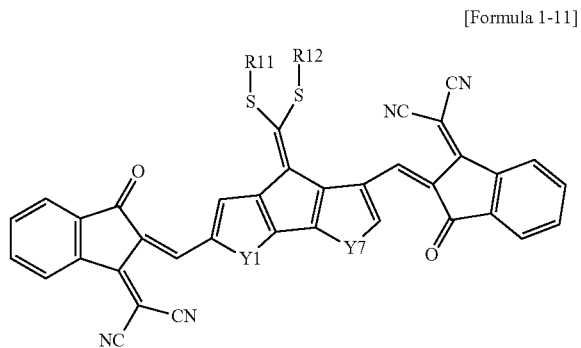

-continued

[Formula 1-13]

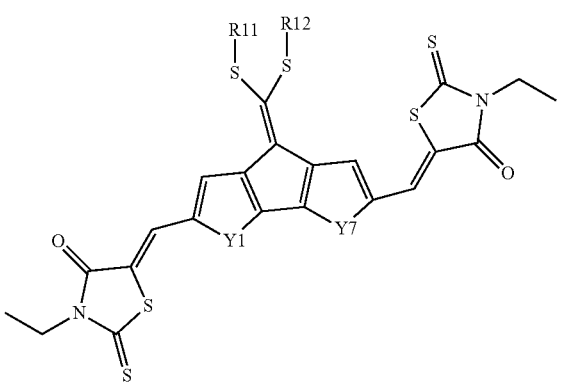

[Formula 1-15]

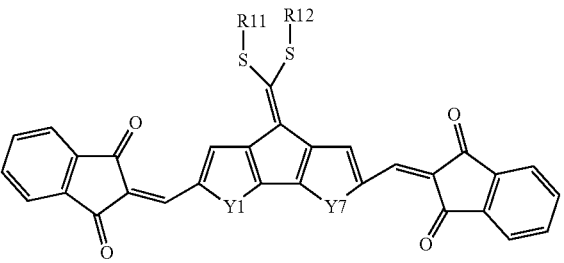

[Formula 1-17]

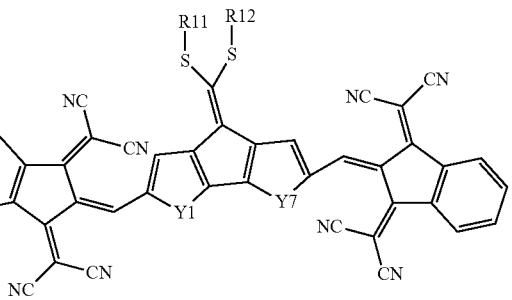

[Formula 1-19]
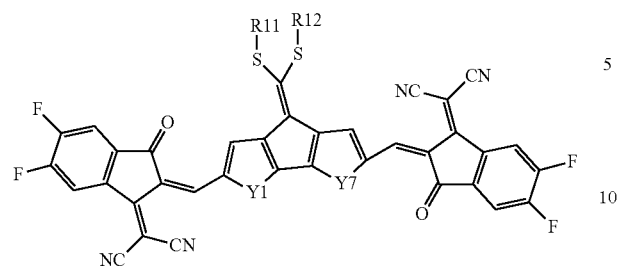
[Formula 1-21]
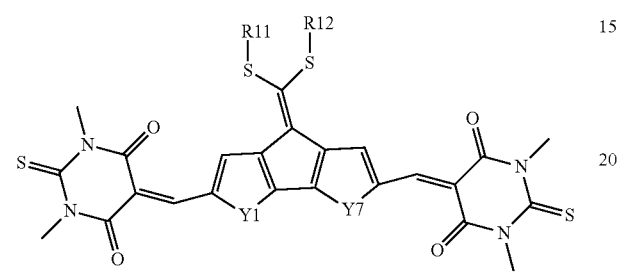
[Formula 1-23]
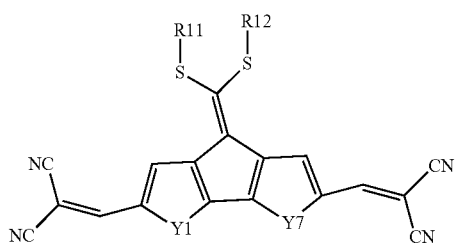
wherein:
Y7 is CRR', NR, O, SiRR', PR, S, GeRR', Se, or Te; and
Y1, R11, R12, R, and R' are the same as those defined in Formula 1.
* * * * *